US 10,045,691 B2

(12) United States Patent
Okada et al.

(10) Patent No.: US 10,045,691 B2
(45) Date of Patent: Aug. 14, 2018

(54) OPHTHALMOLOGIC OBSERVATION APPARATUS USING OPTICAL COHERENCE TOMOGRAPHY

(71) Applicant: KABUSHIKI KAISHA TOPCON, Tokyo (JP)

(72) Inventors: Hiroaki Okada, Saitama (JP); Taisaku Kogawa, Mitaka (JP); Takashi Fujimura, Fujimino (JP); Kohta Fujii, Toda (JP)

(73) Assignee: KABUSHIKI KAISHA TOPCON, Tokyo (JP)

( * ) Notice: Subject to any disclaimer, the term of this patent is extended or adjusted under 35 U.S.C. 154(b) by 50 days.

(21) Appl. No.: 14/650,243

(22) PCT Filed: Nov. 29, 2013

(86) PCT No.: PCT/JP2013/082236
§ 371 (c)(1),
(2) Date: Jun. 5, 2015

(87) PCT Pub. No.: WO2014/087941
PCT Pub. Date: Jun. 12, 2014

(65) Prior Publication Data
US 2015/0335237 A1    Nov. 26, 2015

(30) Foreign Application Priority Data

Dec. 6, 2012 (JP) .................................. 2012-266880

(51) Int. Cl.
*A61B 3/10*     (2006.01)
*A61B 3/14*     (2006.01)
(Continued)

(52) U.S. Cl.
CPC ................. *A61B 3/102* (2013.01); *A61B 3/12* (2013.01); *A61B 3/14* (2013.01); *A61B 3/152* (2013.01)

(58) Field of Classification Search
CPC .. A61B 3/102; A61B 3/12; A61B 3/14; A61B 3/152
(Continued)

(56) References Cited

U.S. PATENT DOCUMENTS 6,377,349 B1    4/2002  Fercher
7,549,746 B2 *  6/2009  Tsukada ................ A61B 3/102
                                                    351/206
(Continued)

FOREIGN PATENT DOCUMENTS

EP       2961311        1/2016
JP       09-276232 A    10/1997
(Continued)

OTHER PUBLICATIONS

Extended European Search Report for EP App No. 13861459.9 dated Jul. 25, 2016, 6 pgs.
(Continued)

Primary Examiner — Zachary Wilkes
(74) Attorney, Agent, or Firm — Procopio, Cory, Hargreaves & Savitch LLP

(57) ABSTRACT

A measuring optical system of an ophthalmologic observation apparatus of an embodiment performs OCT of an eye. An image forming part forms an image based on information acquired by OCT. A preliminary operation performing part performs a plurality of preliminary operations for OCT. Storage stores, for at least one specific preliminary operation among the plurality of preliminary operations, operating condition information including a transferring condition for transferring to a different preliminary operation and a ter-
(Continued)

minating condition for terminating a specific preliminary operation in advance. A controller controls the preliminary operation performing part to commence a specific preliminary operation, controls the preliminary operation performing part to commence a different preliminary operation when the transferring condition of this specific preliminary operation is satisfied, and controls the preliminary operation performing part to terminate this specific preliminary operation when the terminating condition of this specific preliminary operation is satisfied.

10 Claims, 9 Drawing Sheets

(51) Int. Cl.
  *A61B 3/12* (2006.01)
  *A61B 3/15* (2006.01)
(58) Field of Classification Search
  USPC .................. 351/205–206, 209, 221, 215
  See application file for complete search history.

(56) References Cited

U.S. PATENT DOCUMENTS

| | | | |
|---|---|---|---|
| 8,876,292 B2* | 11/2014 | Satake | A61B 3/102 351/206 |
| 9,326,679 B2* | 5/2016 | Takai | A61B 3/102 |
| 2006/0100528 A1 | 5/2006 | Chan et al. | |
| 2009/0027685 A1* | 1/2009 | Abe | A61B 3/102 356/477 |
| 2009/0262359 A1 | 10/2009 | Bajraszewski et al. | |
| 2014/0028975 A1 | 1/2014 | Takai | |

FOREIGN PATENT DOCUMENTS

| | | |
|---|---|---|
| JP | 11-325849 A | 11/1999 |
| JP | 2002-139421 A | 5/2002 |
| JP | 2006-153838 A | 6/2006 |
| JP | 2007-024677 A | 2/2007 |
| JP | 2008-073099 A | 4/2008 |
| JP | 2008-259544 A | 10/2008 |
| JP | 2009-011381 A | 1/2009 |
| JP | 2009-541770 A | 11/2009 |
| JP | 2010-249740 A | 11/2010 |
| JP | 2012-213449 A | 11/2012 |

OTHER PUBLICATIONS

International Search Report dated Dec. 24, 2013, issued for International Application No. PCT/JP2013/082236.

* cited by examiner

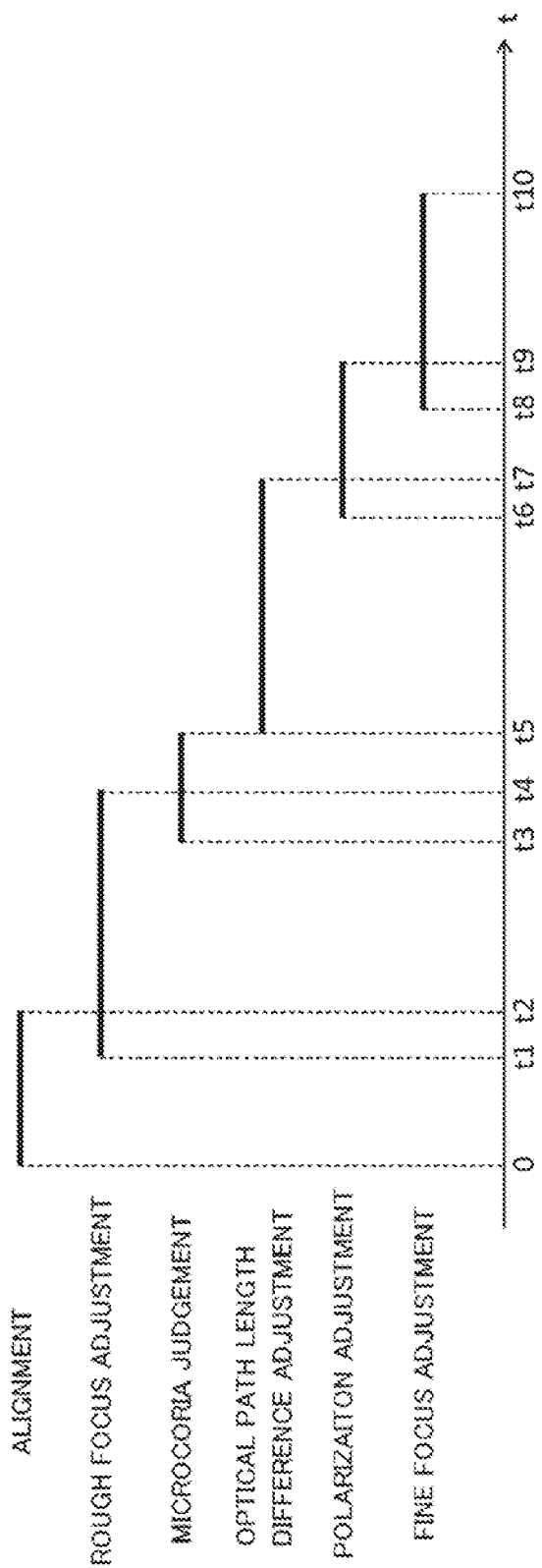

OPHTHALMOLOGIC OBSERVATION APPARATUS USING OPTICAL COHERENCE TOMOGRAPHY

The present application is a National Stage entry of PCT/JP2013/082236, filed on Nov. 29, 2013, which claims priority from Japanese Patent Application No. 2012-266880, filed Dec. 6, 2012, the contents of which are incorporated herein by reference in their entirety.

TECHNICAL FIELD

The present invention relates to an ophthalmologic observation apparatus that acquires images of an eye using optical coherence tomography (OCT).

BACKGROUND TECHNOLOGY

In recent years, OCT for forming images that represent surface and/or internal morphologies of objects by using light beams from laser light sources etc. has attracted attention. Unlike X-ray CT, OCT is noninvasive to human bodies and is therefore expected to be utilized in medical and biological fields in particular. For example, in ophthalmology, apparatuses for forming images of a fundus, a cornea, etc. are in practical stages.

An apparatus disclosed in Patent Document 1 uses so-called "Fourier Domain OCT" technique. More specifically, this apparatus irradiates low-coherence light beam to an object, superposes its reflected light and reference light to generate interference light, and acquires spectral intensity distribution of the interference light and executes Fourier transform to image morphology in a depth direction (z-direction) of the object. Further, this apparatus is provided with a galvano mirror for scanning light beams (signal light) along one direction (x-direction) perpendicular to the z-direction, and forms an image of a desired measurement target region of the object. An image formed by this apparatus is a two-dimensional cross-sectional image along the depth direction (z-direction) and scanning direction (x-direction) of the light beam. Such a technique is specifically called Spectral Domain.

Patent Document 2 discloses a technique that scans signal light in horizontal and vertical directions (x-direction and y-direction) to form two-dimensional cross-sectional images along the horizontal direction, and acquires three-dimensional cross-sectional information of a measured area based on these cross-sectional images to perform imaging. Such three-dimensional imaging techniques include, for example, a method that arranges and displays cross-sectional images along the vertical direction (referred to as stack data etc.), method that executing rendering processing on volume data (voxel data) created from stack data to form a three-dimensional image.

Patent Documents 3 and 4 disclose other types of OCT. An OCT apparatus disclosed in Patent Document 3 scans wavelengths of light irradiated to an object (wavelength sweeping), detects interference light obtained by superposing reflected lights of the respective wavelengths on reference light to acquire spectral intensity distribution, and executes Fourier transform on it to image morphology of an object. Such an OCT technique is called Swept Source etc. Swept Source OCT is a kind of Fourier Domain OCT.

An OCT apparatus disclosed in Patent Document 4 irradiates light having predetermined beam diameter to an object and analyzes components of interference light obtained by superposing reflected light thereof and reference light, thereby forming an image of a cross section of the object orthogonal to irradiating direction of the light. Such an OCT technique is called Full-Field, En-face, etc.

Patent Document 5 discloses an example of OCT application to ophthalmology. Before OCT was applied, a retinal camera, a slit lamp microscope, a scanning laser ophthalmoscope (SLO) etc. were used for observing eyes (see Patent Documents 6 to 8 for example). A retinal camera photographs a fundus by irradiating illumination light onto an eye and receiving reflected light from the fundus. A slit lamp microscope obtains a cross-sectional image of cornea by cutting off a light section of a cornea using slit light. An SLO images morphology of a retinal surface by scanning fundus with laser light and detecting reflected light by high-sensitive elements such as a photomultiplier.

OCT apparatuses have advantages over retinal cameras etc. in that high-definition images may be obtained, cross-sectional and three-dimensional images may be obtained, etc.

Because OCT apparatuses may be used for observing various sites of eyes and is capable of obtaining high-definition images in this way, they have been applied to diagnoses of various ophthalmologic disorders.

PRIOR ART DOCUMENTS

Patent Documents

[Patent Document 1] Japanese Unexamined Patent Application Publication No. H11-325849
[Patent Document 2] Japanese Unexamined Patent Application Publication No. 2002-139421
[Patent Document 3] Japanese Unexamined Patent Application Publication No. 2007-24677
[Patent Document 4] Japanese Unexamined Patent Application Publication No. 2006-153838
[Patent Document 5] Japanese Unexamined Patent Application Publication No. 2008-73099
[Patent Document 6] Japanese Unexamined Patent Application Publication No. H09-276232
[Patent Document 7] Japanese Unexamined Patent Application Publication No. 2008-259544
[Patent Document 8] Japanese Unexamined Patent Application Publication No. 2009-11381

SUMMARY OF THE INVENTION

Problems to be Solved by the Invention

In general, various operations as preliminary operations for OCT are performed for ophthalmologic observation apparatuses using OCT. Specifically, alignment, focus adjustment, optical path length difference adjustment, polarization adjustment, etc. are performed prior to OCT.

In alignment, position matching of an optical system with respect to an eye is performed. In focus adjustment, focus of the optical system is matched with the eye. In optical path length difference adjustment, difference between an optical path length of signal light and an optical path length of reference light is adjusted such that a target site of an eye is imaged adequately. In polarization adjustment, a polarization of signal light and/or a polarization of reference light are/is adjusted so as to improve interference efficiency between the signal light and the reference light.

For ophthalmologic observation apparatuses capable of fundus photography in addition to OCT, microcoria (small pupil) judgement etc. is performed as preliminary operations. Small pupil judgement is a preliminary operation that judges whether an eye is microcoria and that, if the eye is microcoria, places a dedicated diaphragm (a microcoria diaphragm or a crystalline lens diaphragm) in an illumination optical path, applies an electronic mask to an image sensor, or the like.

Preliminary operations as described above are performed one by one in predetermined order. Thus, it takes a certain amount of time for preparation for OCT, thereby imposing a burden on a subject.

One purpose of the present invention is to shorten a time required for preparation for OCT.

Means for Solving the Problem

An ophthalmologic observation apparatus of an embodiment includes: a measuring optical system configured to perform optical coherence tomography of an eye; an image forming part configured to form an image of the eye based on information acquired by the optical coherence tomography; a preliminary operation performing part configured to perform a plurality of preliminary operations for optical coherence tomography; a storage configured to store, for at least one specific preliminary operation among the plurality of preliminary operations, operating condition information including a transferring condition for transferring to a different preliminary operation and a terminating condition for terminating a specific preliminary operation in advance; and a controller configured to control the preliminary operation performing part to commence a specific preliminary operation, control the preliminary operation performing part to commence a different preliminary operation when the transferring condition of this specific preliminary operation is satisfied, and control the preliminary operation performing part to terminate this specific preliminary operation when the terminating condition of this specific preliminary operation is satisfied.

Effect of the Invention

According to the present invention, it is possible to shorten a time required for preparation for OCT.

BRIEF DESCRIPTION OF THE DRAWINGS

FIG. 7 is a schematic diagram for explaining an operation example of an ophthalmologic observation apparatus according to an embodiment.

MODE FOR CARRYING OUT THE INVENTION

Examples of embodiments of an ophthalmological imaging apparatus according to the present invention are described in detail with reference to drawings. An ophthalmologic observation apparatus according to the present invention uses OCT to form cross-sectional images and/or three-dimensional images of an eye. In this specification, images acquired by OCT are sometimes referred to as OCT images. Also, measurement actions for forming OCT images are sometimes referred to as OCT (measurement). The contents disclosed in the documents cited in this specification may be applied to the following embodiments.

In the following embodiments, configurations in which Fourier Domain OCT is employed are described in detail. Particularly, ophthalmologic observation apparatuses described later are capable of obtaining OCT image by means of Spectral Domain OCT and of obtaining fundus images as the apparatus disclosed in Patent Document 5. Configurations according to the present invention may be applied to ophthalmologic observation apparatuses of any type other than Spectral Domain (for example, Swept Source OCT). The following embodiments describe apparatuses as a combination of OCT apparatus and retinal camera; however, an ophthalmologic imaging apparatus other than a retinal camera such as SLO, slit lamp microscope, ophthalmologic operation microscope, etc. may be combined with an OCT apparatus including configurations according to embodiments. Alternatively, configurations according to embodiments may be provided in a monofunctional OCT apparatus.

[Configurations]

Figure 1:
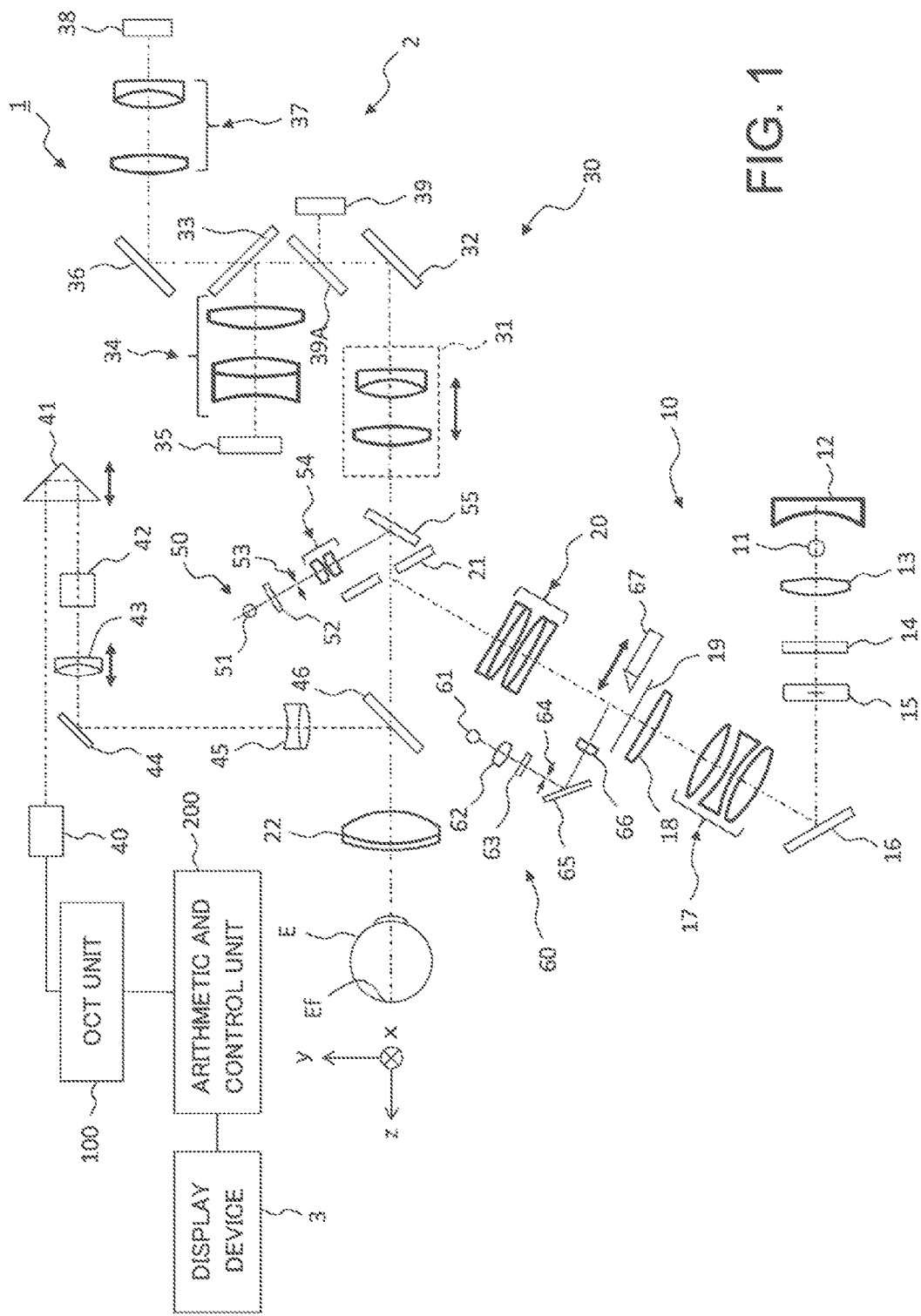
FIG. 1 is a schematic diagram illustrating a configuration example of an ophthalmologic observation apparatus according to an embodiment.
Figure 2:
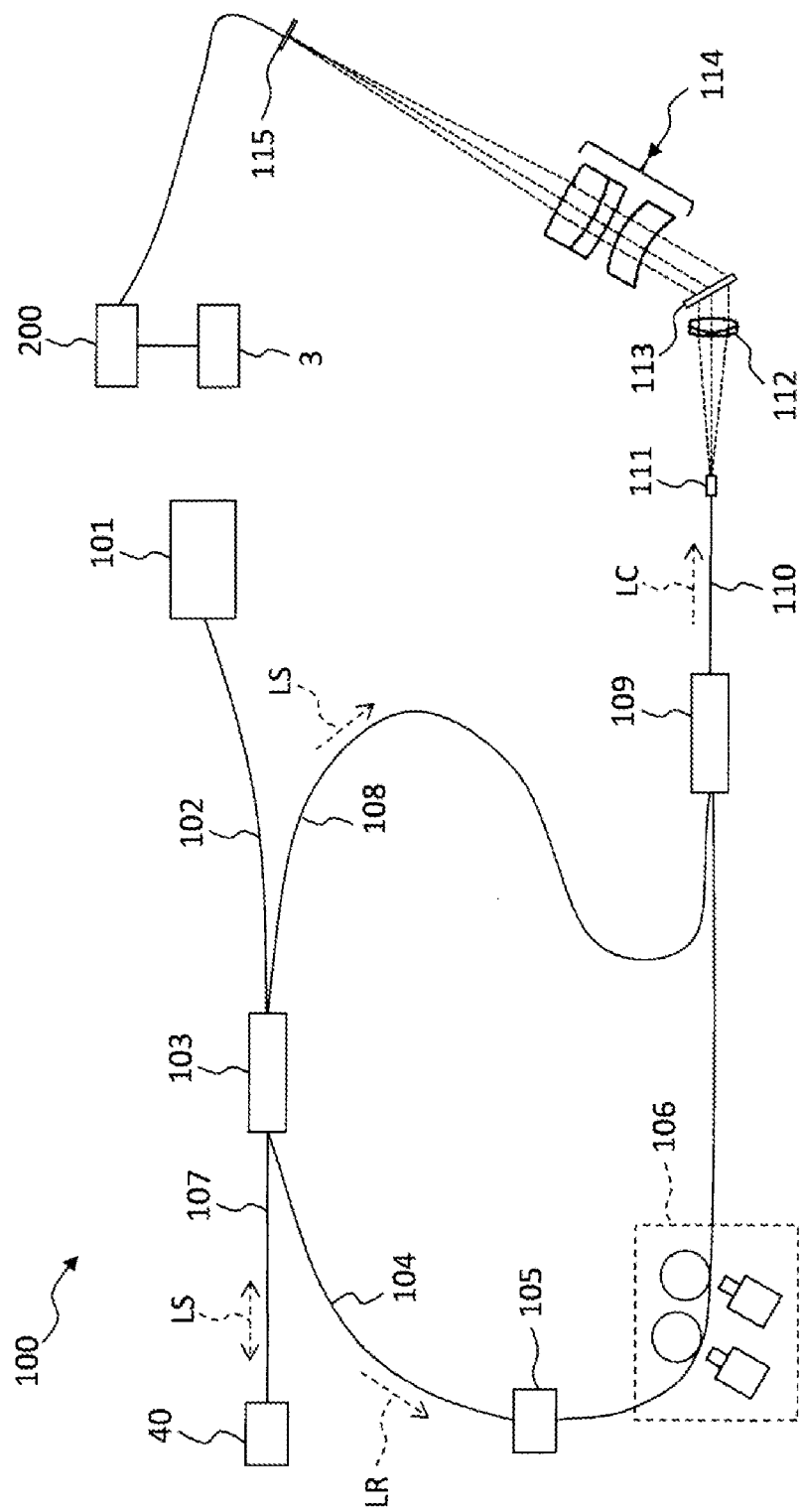
FIG. 2 is a schematic diagram illustrating a configuration example of an ophthalmologic observation apparatus according to an embodiment.

As shown in FIG. 1 and FIG. 2, an ophthalmologic observation apparatus 1 includes a retinal camera unit 2, an OCT unit 100 and an arithmetic and control unit 200. The retinal camera unit 2 includes almost the same optical systems as a conventional retinal camera. The OCT unit 100 is provided with optical systems for obtaining fundus OCT images. The arithmetic and control unit 200 includes a computer that executes various arithmetic processing, control processing, etc.

[Retinal Camera Unit]

The retinal camera unit 2 shown in FIG. 1 is provided with an optical system for obtaining a two-dimensional image (fundus image) representing surface morphology of a fundus Ef of an eye E. Fundus image include observation images, photographed images, etc. An observation image is, for example, a monochromatic moving image formed at a predetermined frame rate using near-infrared light. A photographed image may be, for example, a color image captured by flashing visible light or a monochromatic still image captured using near-infrared light or visible light as illumination light. The retinal camera unit 2 may also capture other types of images such as fluorescein angiography images, indocyanine green fluorescent images and autofluorescent images.

The retinal camera unit 2 is provided with a chin rest and forehead placement for supporting a subject's face. Moreover, the retinal camera unit 2 is provided with an illumination optical system 10 and imaging optical system 30. The illumination optical system 10 irradiates illumination light to the fundus Ef. The imaging optical system 30 guides fundus-reflected light of illumination light to imaging devices (CCD image sensors 35, 38 (sometimes referred to simply as CCD)). Further, the imaging optical system 30 guides signal light from the OCT unit 100 to the fundus Ef and guides the signal light traveled via the fundus Ef to the OCT unit 100.

An observation light source 11 of the illumination optical system 10 includes a halogen lamp, for example. Light (observation illumination light) output from the observation light source 11 is reflected by a reflection mirror 12 with a curved reflection surface, passes through a condenser lens 13 and becomes near-infrared light after passing through a visible cut filter 14. Further, the observation illumination light is once converged near an imaging light source 15, reflected by a mirror 16 and passes through relay lenses 17 and 18, a diaphragm 19 and a relay lens 20. Then, the observation illumination light is reflected by a peripheral part (region surrounding an aperture part) of an aperture mirror 21, transmitted through a dichroic mirror 46 and refracted by an objective lens 22, thereby illuminating the fundus Ef. LED (Light Emitting Diode) may be used as the observation light source.

The fundus-reflected light of the observation illumination light is refracted by the objective lens 22, transmitted through the dichroic mirror 46, passes through the aperture part formed in the center region of the aperture mirror 21, transmitted through a dichroic mirror 55, travels through a focusing lens 31 and reflected by a mirror 32. Further, the fundus-reflected light is transmitted through a half-mirror 39A, reflected by a dichroic mirror 33 and forms an image on a light-receiving surface of the CCD 35 by a condenser lens 34. The CCD 35 detects the fundus-reflected light at a preset frame rate, for example. An image (observation image) based on the fundus-reflected light detected by the CCD 35 is displayed on a display device 3. When the imaging optical system 30 is focused on the anterior eye part, the observation image of the anterior eye part of the eye E is displayed.

The imaging light source 15 includes a xenon lamp, for example. Light (imaging illumination light) output from the imaging light source 15 is irradiated to the fundus Ef through the same route as the observation illumination light. The fundus-reflected light of the imaging illumination light is guided to the dichroic mirror 33 via the same route as the observation illumination light, transmitted through the dichroic mirror 33, reflected by a mirror 36 and forms an image on a light-receiving surface of the CCD 38 by a condenser lens 37. An image (photographed image) based on the fundus-reflected light detected by the CCD 38 is displayed on the display device 3. The display device 3 for displaying observation image and display device 3 for displaying photographed image may be the same or different. When similar photography is carried out by illuminating the eye E with infrared light, infrared photographed image is displayed. LED may be used as the imaging light source.

The illumination optical system 10 includes a small pupil diaphragm insertible into and removable from an optical path. The small pupil diaphragm is inserted into the optical path when the eye E is microcoria. The small pupil diaphragm is arranged in the optical path as the diaphragm 19, for example. When a pupil diameter of the eye E is normal, a diaphragm (normal pupil diaphragm) used for photography of the eye E with normal pupil diameter is arranged in the optical path as the diaphragm 19. In such a case, the diaphragm includes the normal pupil diaphragm and the small pupil diaphragm that can be selectively placed in the optical path.

An LCD (Liquid Crystal Display) 39 displays fixation targets, targets for visual-acuity measurement, etc. The fixation target is a visual target (index) for fixating the eye E and used in fundus photography, OCT, etc.

Part of light output from the LCD 39 is reflected by the half-mirror 39A, reflected by the mirror 32, travels through the focusing lens 31 and the dichroic mirror 55, passes through the aperture part of the aperture mirror 21, transmitted through the dichroic mirror 46, refracted by the objective lens 22, and projected onto the fundus Ef.

By changing a display position of the fixation target on the LCD 39's screen, a fixation position of the eye E may be changed. Examples of fixation positions of the eye E include position for acquiring a macula-centered image, position for acquiring optic-papilla-centered image, position for acquiring fundus-center image (centered at a location between macula and optic papilla), etc., as in conventional retinal cameras. Display positions of fixation targets may be changed arbitrarily.

As with conventional retinal cameras, the retinal camera unit 2 includes an alignment optical system 50 and a focus optical system 60. The alignment optical system 50 generates an index (target, alignment index) for matching a position of the optical system with the eye E (that is, for performing alignment). The alignment optical system 50 is an example of a "first projection optical system" and the alignment index is an example of a "first index". The focus optical system 60 generates an index (target, split index) for adjusting focus on the eye Ef. The focus optical system 60 is an example of a "second projection optical system" and the split index is an example of a "second index".

Light (alignment light) output from an LED 51 of the alignment optical system 50 passes through diaphragms 52 and 53 and a relay lens 54, is reflected by the dichroic mirror 55, passes through the aperture part of the aperture mirror 21, is transmitted through the dichroic mirror 46 and is projected on the cornea of the eye E by the objective lens 22.

Cornea-reflected light of the alignment light passes through the objective lens 22, dichroic mirror 46 and aperture part, and then part of the cornea-reflected light is transmitted through the dichroic mirror 55, passes through the focusing lens 31, reflected by the mirror 32, transmitted through the half-mirror 39A, reflected by the dichroic mirror 33, and projected on the light-receiving surface of the CCD 35 by the condenser lens 34. An image (alignment index) captured by the CCD 35 is displayed on the display device 3 together with an observation image. The user may conduct manual alignment while observing the alignment index. Although details are described later, the arithmetic and control unit 200 may perform alignment by analyzing a position of the alignment index and moving the optical system (automatic alignment).

In order to perform focus adjustment, a reflection surface of a reflection rod 67 is obliquely disposed in an optical path of the illumination optical system 10. Light (focus light) output from an LED 61 of the focus optical system 60 passes through a relay lens 62, is split into two light fluxes by a split index plate 63, passes through a two-hole diaphragm 64, is reflected by a mirror 65, is formed an image on the reflection surface of the reflection rod 67 by a condenser lens 66 and then is reflected. Further, the focus light passes through the relay lens 20, is reflected by the aperture mirror 21, is transmitted through the dichroic mirror 46, is refracted by the objective lens 22 and is projected on the fundus Ef.

Fundus-reflected light of the focus light passes through the same route as the cornea-reflected light of the alignment light and is detected by the CCD 35. An image (split index) captured by the CCD 35 is displayed on the display device 3 together with an observation image. The user may conduct manual focus adjustment while observing the split index. Although details are described later, the arithmetic and control unit 200 may perform focus adjustment by analyzing a position of the split index and moving the focusing lens 31 and the focus optical system 60 (automatic focusing).

An optical path for OCT is branched from an optical path for fundus photography by the dichroic mirror 46. The dichroic mirror 46 reflects light of wavelength bands for OCT and transmits light for fundus photography. The OCT optical path includes a collimator lens unit 40, an optical path length changing part 41, a galvano scanner 42, a focusing lens 43, a mirror 44 and a relay lens 45 in this order from the OCT unit 100.

The optical path length changing part 41 is movable in an optical axis direction (direction indicated by an arrow in FIG. 1) to change an optical length of the OCT optical path (signal light path). A difference between an optical path length of the signal light path and an optical path length of a reference light path (optical path length difference) is changed by changing the optical path length of the signal light path. The change in the optical path length difference may be used for correction of an optical path length in accordance with an axial length of the eye E, adjustment of an interference state, etc. The optical path length changing part 41 includes a corner cube and a mechanism for moving the corner cube, for example. The optical path length changing part 41 is an example of an "optical path length difference changing part".

A configuration of the optical path length difference changing part is not limited to this. For example, the optical path length of the reference light path may be changed by providing a reflection mirror (reference mirror) in the reference light path and moving the reference mirror in a traveling direction of the reference light. Further, the optical path length of the signal light may be changed by moving the optical system contributing to OCT (measuring optical system) with respect to the eye. Generally, the optical path length difference changing part includes an arbitrary configuration that is capable of changing the optical path length(s) of the signal light path and/or the reference light path.

The galvano scanner 42 changes a travelling direction of light (signal light) guided along the OCT optical path. Accordingly, the fundus Ef is scanned by the signal light. The galvano scanner 42 includes a galvano mirror for scanning the signal light in the x-direction, a galvano mirror for scanning the signal light in the y-direction, and a mechanism for independently driving these. Thereby, the signal light may be scanned in an arbitrary direction in the xy-plane.

[OCT Unit]

A configuration example of the OCT unit 100 is explained with reference to FIG. 2. The OCT unit 100 is provided with an optical system for obtaining OCT images of the fundus Ef. This optical system includes a configuration similar to a conventional Spectral Domain OCT apparatus. That is, this optical system is configured to split low-coherence light into signal light and reference light, superpose the signal light returned form the fundus Ef with the reference light having traveled through the reference light path to generate interference light, and detect spectral components of the interference light. Results of the detection (detection signal) are transmitted to the arithmetic and control unit 200.

When Swept Source OCT is applied, a wavelength-sweeping light source (wavelength tunable light source) is provided instead of a low-coherence light source while an optical member for spectrally decomposing interference light is not provided. In general, any known a technique in accordance with OCT type may be arbitrarily applied for a configuration of the OCT unit 100.

A light source unit 101 outputs broadband, low-coherence light L0. The low-coherence light L0, for example, contains a near-infrared wavelength band (about 800-900 nm) and has a temporal coherence length of about tens of micrometer. It is possible to use wavelength bands invisible for human eyes such as near-infrared light having center wavelength of about 1040-1060 nm as the low-coherence light L0.

The light source unit 101 includes light-emitting device, such as SLD (super luminescent diode), LED, SOA (Semiconductor Optical Amplifier), etc.

The low-coherence light L0 output from the light source unit 101 is guided to a fiber coupler 103 through an optical fiber 102, and split into signal light LS and reference light LR.

The reference light LR is guided to an optical attenuator 105 through an optical fiber 104. Using any known technology, the arithmetic and control unit 200 controls the optical attenuator 105 for automatically adjusting light quantity (light intensity) of the reference light LR guided through the optical fiber 104. The reference light LR whose light quantity has been adjusted by the optical attenuator 105 is guided through the optical fiber 104 and reaches a polarization controller 106.

The polarization controller 106 applies stress from outside to the optical fiber 104 of loop-form to change polarization of the reference light LR being guided in the optical fiber 104, for example. A configuration of the polarization controller 106 is not limited to this and arbitrary known technology may be applied. The reference light LR whose polarization has been adjusted by the polarization controller 106 is guided to an optical coupler 109.

The polarization controller 106 is an example of a "polarization changing part". The polarization changing part may change polarization of signal light LS. In general, the polarization changing part changes polarization of signal light LS and/or reference light LR. With this, polarization of the signal light LS and polarization of the reference light LR are matched with each other, thereby improving interference efficiency.

The signal light LS generated by the fiber coupler 103 is guided through the optical fiber 107 and converted into a parallel light flux by the collimator lens unit 40. Further, the signal light LS travels through the optical path length changing part 41, the galvano scanner 42, the focusing lens 43, the mirror 44 and the relay lens 45, and reaches the dichroic mirror 46. Then, the signal light LS is reflected by the dichroic mirror 46, refracted by the objective lens 22 and projected onto the fundus Ef. The signal light LS is scattered (reflected) at various depth positions of the fundus Ef. Back-scattered light of the signal light LS from the fundus Ef travels along the same route as the outward way in the opposite direction to the fiber coupler 103, and reaches the fiber coupler 109 through an optical fiber 108.

The fiber coupler 109 superposes the back-scattered light of the signal light LS and the reference light LR having passed through the optical fiber 104. Interference light LC thus generated is guided by an optical fiber 110 and output from an exit end 111. Further, the interference light LC is converted into a parallel light flux by a collimator lens 112, spectrally divided (spectrally decomposed) by a diffraction grating 113, converged by a condenser lens 114, and projected onto a light-receiving surface of a CCD image sensor 115. Although the diffraction grating 113 shown in FIG. 2 is of transmission type, any other kinds of spectrally decomposing elements (such as reflection type) may be used.

The CCD image sensor 115 is for example a line sensor. The CCD image sensor 115 detects respective spectral components of spectrally-decomposed interference light LC and converts the detected components into electric charges. The CCD image sensor 115 accumulates the electric charges to generate detection signals and transmits the detection signals to the arithmetic and control unit 200.

Although Michelson-type interferometer is employed in the embodiment, any type of interferometer such as a Mach-Zehnder-type may be employed as necessary. Instead of CCD, other types of image sensors such as CMOS (Complementary Metal Oxide Semiconductor) may be used. Further, when Swept Source OCT is applied, the diffraction grating 113 is not required and a balanced photodiode is provided instead of the CCD image sensor 115.

[Arithmetic and Control Unit]

A configuration of the arithmetic and control unit 200 is described. The arithmetic and control unit 200 analyzes detection signals input from the CCD image sensor 115 to form OCT images of the fundus Ef. Arithmetic processing for this may be the same as conventional Spectral Domain OCT apparatus.

The arithmetic and control unit 200 controls each part of the retinal camera unit 2, the display device 3 and the OCT unit 100. For example, the arithmetic and control unit 200 displays OCT images of the fundus Ef on the display device 3.

As controls of the retinal camera unit 2, the arithmetic and control unit 200 executes: action controls of the observation light source 101, the imaging light source 103 and the LED's 51 and 61; action control of the LCD 39; movement controls of the focusing lenses 31 and 43; movement control of the reflection rod 67; movement control of the focus optical system 60; movement control of the optical path length changing part 41; action control of the galvano scanner 42; etc.

As controls of the OCT unit 100, the arithmetic and control unit 200 executes: action control of the light source unit 101; action control of the optical attenuator 105; action control of the polarization controller 106; action control of the CCD image sensor 115; etc.

The arithmetic and control unit 200 includes a microprocessor, RAM, ROM, hard disk drive, communication interface, etc. as with conventional computers. Storage devices such as hard disk drive store computer programs for controlling the ophthalmologic observation apparatus 1. The arithmetic and control unit 200 may include various circuit boards such as circuit boards for OCT-image formation. The arithmetic and control unit 200 may include operation devices (input devices) such as a keyboard, mouse and/or display device such as LCD.

The retinal camera unit 2, display device 3, OCT unit 100 and arithmetic and control unit 200 may be integrally configured (that is, provided within a single case) or separately configured in two or more cases.

[Control System]

Figure 3:
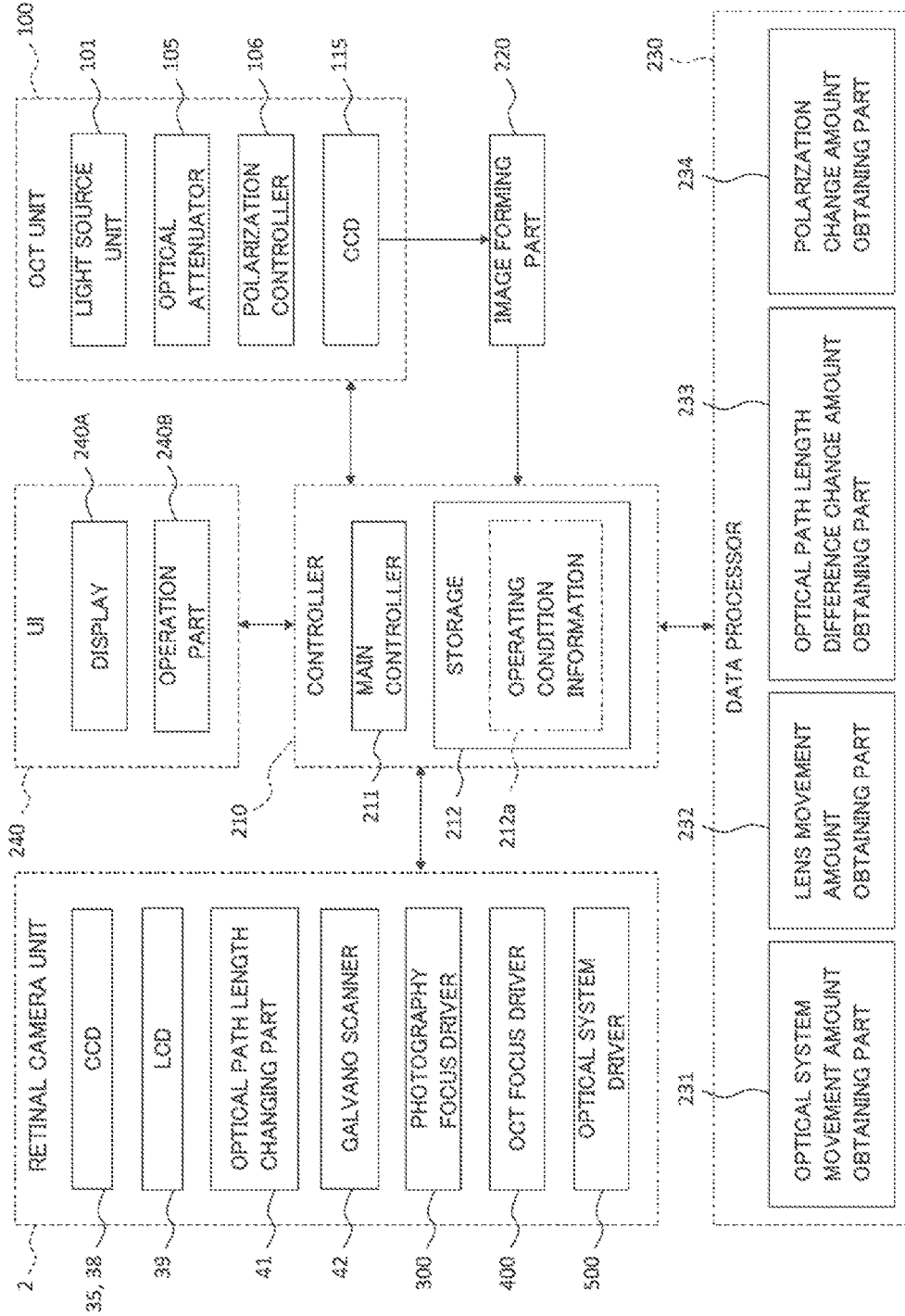
FIG. 3 is a schematic block diagram illustrating a configuration example of an ophthalmologic observation apparatus according to an embodiment.

A configuration of a control system of the ophthalmologic observation apparatus 1 is described with reference to FIG. 3.

(Controller)

A controller 210 is the center of the control system of the ophthalmologic observation apparatus 1. The controller 210 includes the above microprocessor, RAM, ROM, hard disk drive and communication interface, etc., for example. The controller 210 includes a main controller 211 and a storage 212.

(Main Controller)

The main controller 211 performs various controls as described above. In particular, the main controller 211 controls the optical path length changing part 41, the galvano scanner 42, focusing lens 43 as well as the focus optical system 60 (photography focus driver 300), the focusing lens 43 (OCT focus driver 400), the entirety of the optical systems (optical system driver 500), etc. in the retinal camera unit 2. Further, the main controller 211 controls the light source unit 101, the optical attenuator 105, the polarization controller 106, etc. in the OCT unit 100.

The photography focus driver 300 moves the focusing lens 31 in a direction of the optical axis of the imaging optical system 30 and moving the focus optical system 60 in a direction of the optical axis of the illumination optical system 10. With this, a focus position of the imaging optical system 30 is varied. The photography focus driver 300 may include a mechanism for moving the focusing lens 31 and a mechanism for moving the focus optical system 60 separately. The photography focus driver 300 is controlled when focus adjustment is performed, for example.

The OCT focus driver 400 moves the focusing lens 43 in a direction of the optical axis of the signal light path. With this, a focus position of the signal light LS is varied. The focus position of the signal light LS corresponds to a depth position (z-position) of a beam waist of the signal light LS. The OCT focus driver 400 is an example of a "second driver".

The optical system driver 500 three-dimensionally moves optical systems provided in the retinal camera unit 2. Such control is used for alignment and tracking. Tracking is an operation for moving optical systems in accordance with eye movement of the eye E. When tracking is performed, alignment and focus adjustment are performed in advance. Tracking is a function to maintain adequate positional relationship in which alignment and focusing are suitable by causing positions of the optical systems to follow eye movement. The optical system driver 500 is an example of a "first driver".

The main controller 211 executes processing of writing data into the storage 212 and processing of reading out data from the storage 212.

(Storage)

The storage 212 stores various kinds of data. Data stored in the storage 212 may include OCT image data, fundus image data, eye information, etc., for example. The eye information includes information on subjects such as patient ID's, names and information on eyes such as identification of left/right eye. The storage 212 stores various programs and data for operating the ophthalmologic observation apparatus 1.

The storage 212 of this embodiment stores operating condition information 212a in advance. The operating condition information 212a is described. The ophthalmologic observation apparatus 1 performs a plurality of preliminary operations prior to OCT measurement. Examples of preliminary operations include alignment, rough focus adjustment, microcoria judgement, optical path length difference adjustment, polarization adjustment, fine focus adjustment, and so on. The plurality of preliminary operations is carried out in a preset order. In the present embodiment, it is assumed that they are performed in the abovementioned order. However, types and order of preliminary operations are not limited to the above and may be arbitrary.

Here, the rough focus adjustment is focus adjustment performed using the split index described above. Note that the rough focus adjustment may be performed by determining a position of the focusing lens 43 based on information that associates eye refractive powers with positions of the focusing lens 43 and a measured value of a refractive power of the eye. On the other hand, fine focus adjustment is focus adjustment performed based on interference sensitivity of OCT. For example, the fine focus adjustment may be performed by: finding a position of the focusing lens 43 so as to maximize interference sensitivity by means of carrying out OCT of the eye E to obtain interference signals and monitoring interference intensity (interference sensitivity); and moving the focusing lens 43 to the position found.

The operating condition information 212a includes a transferring condition and a terminating condition for at least one (referred to as a specific preliminary operation) of the preliminary operations. The transferring condition is a condition for transferring from a concerned specific preliminary operation to a different preliminary operation, in other words, a condition for commencing the different preliminary operation while continuously performing the specific preliminary operation. The terminating condition is a condition for terminating the specific preliminary operation. The transferring condition is more moderate than the terminating condition in general. That is, they are set such that the terminating condition is not satisfied unless the transferring condition is satisfied. Note that the transferring condition and the terminating condition may be the same in some cases.

In the alignment, a movement amount of the measuring optical system is obtained by analyzing a front image of the eye E (observation image of the anterior eye part) as described later. Further, the operating condition information 212a includes a first threshold of the movement amount of the measuring optical system as the transferring condition and a second threshold that is smaller than the first threshold as the terminating condition.

In the rough focus adjustment, a movement amount of the focusing lens 43 is obtained by analyzing a front image of the eye E (observation image of the anterior eye part) as described later. Further, the operating condition information 212a includes a first threshold of the movement amount of the focusing lens 43 as the transferring condition and a second threshold that is smaller than the first threshold as the terminating condition.

In the optical path length difference adjustment, a change amount of an optical path length difference between the signal light path and the reference light path is obtained by analyzing detection results of interference light LC from the measuring optical system as described later. Further, the operating condition information 212a includes a first threshold of the change amount of the optical path length difference as the transferring condition and a second threshold that is smaller than the first threshold as the terminating condition.

In polarization adjustment, a change amount of a polarization state of signal light LS and/or a change amount of a polarization state of the reference light LR are/is obtained by analyzing detection results of interference light LC from the measuring optical system as described later. Further, the operating condition information 212a includes a first threshold(s) of the change amount(s) of the polarization state(s) as the transferring condition and a second threshold(s) that is (are) smaller than the first threshold(s) as the terminating condition.

Note that it is not necessary to prepare the operating condition information 212a for all of these preliminary operations in embodiments; however, the operating condition information 212a may be prepared for any one or two or more among these preliminary operations.

Regarding the microcoria judgement, since it is performed almost instantly and a threshold is not required for it, the operating condition information 212a is not necessarily prepared. However, since the microcoria judgement includes stepwise actions such as acquisition of a front image (anterior eye part image) of the eye E, judgement processing, control of the diaphragm 19, etc., it is possible to set completion of any (such as the acquisition of a front image) of the actions in the middle as the transferring condition and set completion of the last action (such as the control of the diaphragm 19) as the terminating condition.

Regarding the fine focus adjustment, since it is the last preliminary operation performed in this embodiment, the operating condition information 212a is not necessarily prepared. Note that when other preliminary operation(s) is (are) performed after the fine focus adjustment, the operating condition information 212a may be prepared for the fine focus adjustment. For example, a first threshold of the interference intensity may be set as the transferring condition and a second threshold that is greater than the first threshold may be set as the terminating condition.

(Image Forming Part)

An image forming part 220 forms cross-sectional image data of the fundus Ef based on detection signals from the CCD image sensor 115. Like conventional Spectral Domain OCT, this processing includes noise elimination (noise reduction), filtering, dispersion compensation, FFT (Fast Fourier Transform), etc. For OCT apparatuses of other types, the image forming part 220 executes known processing in accordance with a type applied.

The image forming part 220 may include the aforementioned circuit boards, for example. "Image data" and an "image" based on this image data may be identified with each other in this specification.

(Data Processor)

A data processor 230 processes data acquired by photography and OCT measurement of the eye E. For example, the data processor 230 executes various image processing and analysis on images formed by the image forming part 220. For example, the data processor 230 executes various corrections such as brightness correction of images etc. Moreover, the data processor 230 executes various image processing and analysis on images obtained by the retinal camera unit 2 (fundus images, anterior eye part images, etc.).

The data processor 230 executes known image processing such as interpolation that interpolates pixels between cross-sectional images to form three-dimensional image data of the fundus Ef. Three-dimensional image data refers to image data whose pixel positions are defined by a three-dimensional coordinate system. Three-dimensional image data may be image data composed of three-dimensionally arranged voxels, for example. Such image data is referred to as volume data, voxel data, etc. For displaying an image based on volume data, the data processor 230 executes rendering processing (such as volume rendering, MIP (Maximum Intensity Projection), etc.) on the volume data to form image data of a pseudo three-dimensional image taken from a specific view direction. This pseudo three-dimensional image is displayed on a display device such as a display 240A.

It is also possible to form stack data of cross-sectional images as three-dimensional image data. Stack data is image data obtained by three-dimensionally arranging cross-sectional images acquired along scanning lines, wherein the arrangement is based on positional relationship of the scanning lines. That is, stack data is image data obtained by representing, with a three-dimensional coordinate system, cross-sectional images originally defined in respective two-dimensional coordinate systems (in other words, by embedding them into a three-dimensional space).

The data processor 230 includes an optical system movement amount obtaining part 231, a lens movement amount obtaining part 232, an optical path length difference change amount obtaining part 233, and a polarization change amount obtaining part 234. Here, the optical system movement amount obtaining part 231 relates to the alignment, the lens movement amount obtaining part 232 relates to the rough focus adjustment, the optical path length difference change amount obtaining part 233 relates to the optical path length difference adjustment, and the polarization change amount obtaining part 234 relates to the polarization adjustment. All of these functional portions are not necessarily provided in the data processor 230 and it is sufficient that only a functional portion(s) relating to a preliminary operation(s) to be performed in an embodiment is (are) provided. When other preliminary operation(s) is (are) performed in an embodiment, a functional portion(s) relating to this preliminary operation(s) is (are) provided.

The optical system movement amount obtaining part 231 is described. When performing the alignment, the ophthalmologic observation apparatus 1 acquires a front image of the eye E by photographing the eye E (anterior eye part) on which the alignment index is being projected. The front image is a moving image with a preset frame rate. The optical system movement amount obtaining part 231 analyzes (frames of) the front image to obtain a movement amount of the measuring optical system required for achieving a suitable alignment state. The optical system movement amount obtaining part 231 is an example of a "first obtaining part".

Information obtained by the optical system movement amount obtaining part 231 is not limited to a movement amount of the measuring optical system itself. For example, the optical system movement amount obtaining part 231 may obtain information that is substantially equivalent to a movement amount of the measuring optical system such as control contents (the number of pulses transmitted, or the like) of the optical system driver 500, information obtained in the middle of processing of acquiring the movement amount (shift amount of alignment, etc.) or the like.

Figure 4A:
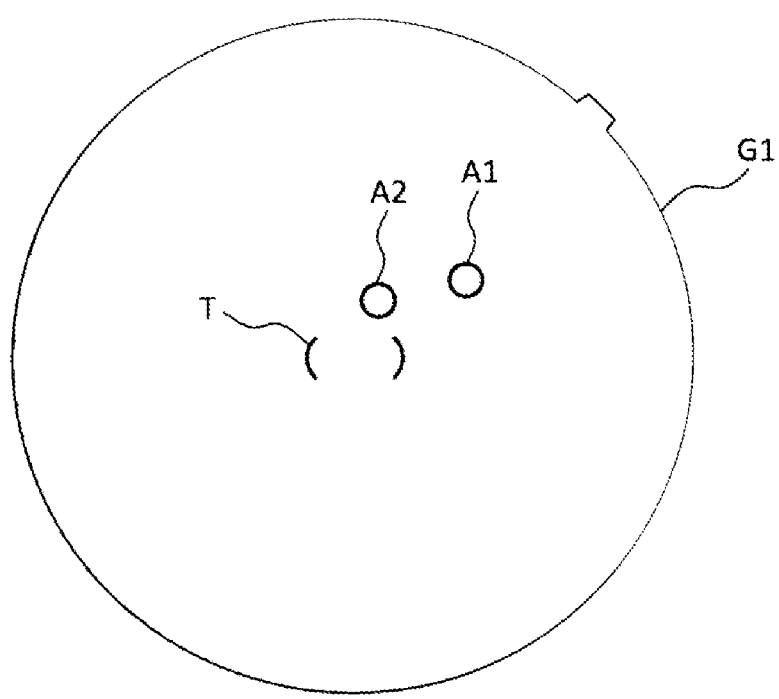
FIG. 4A is a schematic diagram for explaining processing performed by an ophthalmologic observation apparatus according to an embodiment.
Figure 4B:
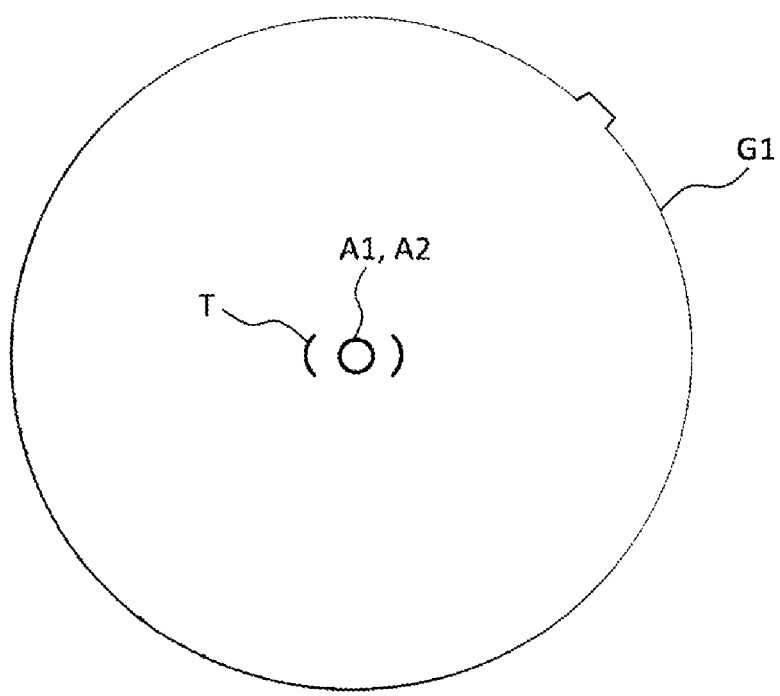
FIG. 4B is a schematic diagram for explaining processing performed by an ophthalmologic observation apparatus according to an embodiment.

An example of processing performed by the optical system movement amount obtaining part 231 is descried. A front image input into the optical system movement amount obtaining part 231 depicts the alignment index. An example of an aspect of depiction of the alignment index is illustrated in FIGS. 4A and 4B. An image of the eye E is omitted in FIGS. 4A and 4B.

Two images (alignment index images) A1 and A2 of the alignment index are depicted as bright points in a front image G1 of the eye E illustrated in FIG. 4A. Further, the main controller 211 overlays a target image T with a parenthesis shape that indicates a target position of alignment in the center location of the front image G1.

If alignment is displaced in the xy-directions with respect to the eye E, the alignment index images A1 and A2 are depicted at locations apart from the target image T. Also, if alignment is displaced in the z-direction, the alignment index images A1 and A2 are depicted at different locations from each other. If alignment is appropriate in all the xyz-directions, the alignment index images A1 and A2 are overlapped with each other and depicted inside the target image T as illustrated in FIG. 4B.

A displacement (amount and direction thereof) of the alignment index images A1 and A2 from the target image T indicates misalignment (amount and direction thereof) in the xy-directions. A displacement (amount and direction thereof) between the two alignment index images A1 and A2 indicates misalignment (amount and direction thereof) in the z-direction.

The optical system movement amount obtaining part 231 analyzes the front image G1 to find a shift of alignment, and obtain a movement amount of the optical system such that the shift is cancelled. Such processing may be performed in the following way, for example. To begin with, the optical system movement amount obtaining part 231 specifies image regions corresponding to the alignment index images A1 and A2 based on pixel information (such as brightness values, etc.) of the front image G1. Next, the optical system movement amount obtaining part 231 specifies a characteristic position (center, barycenter, etc.) of the each image region specified. Then, the optical system movement amount obtaining part 231 finds a displacement of the characteristic position of the each image region from the center of the target image T. Next, the optical system movement amount obtaining part 231 calculates a shift of alignment based on the found displacements and obtains a movement amount of the optical system such that this alignment shift is cancelled. Note that the optical system movement amount obtaining part 231 may be configured to: store information that associates displacements of alignment index images defined in a coordinate system of a front image with alignment shifts defined in the real space in advance; and refer to such association information to find a shift of alignment.

The lens movement amount obtaining part 232 is described. When performing the rough focus adjustment, the ophthalmologic observation apparatus 1 acquires a front image of the eye E by photographing the fundus Ef on which the split index (focusing index) is being projected. The front image is a moving image with a preset frame rate. The lens movement amount obtaining part 232 analyzes (frames of) the front image to obtain a movement amount of the focusing lens 43 required for achieving a suitable focus state. The lens movement amount obtaining part 232 is an example of a "second obtaining part".

Information obtained by the lens movement amount obtaining part 232 is not limited to a movement amount of the focusing lens 43 itself. For example, the lens movement amount obtaining part 232 may obtain information that is substantially equivalent to a movement amount of the focusing lens 43 such as control contents (the number of pulses transmitted, or the like) of the OCT focus driver 400, information obtained in the middle of processing of acquiring the movement amount (shift amount of focus, etc.) or the like.

Figure 5A:
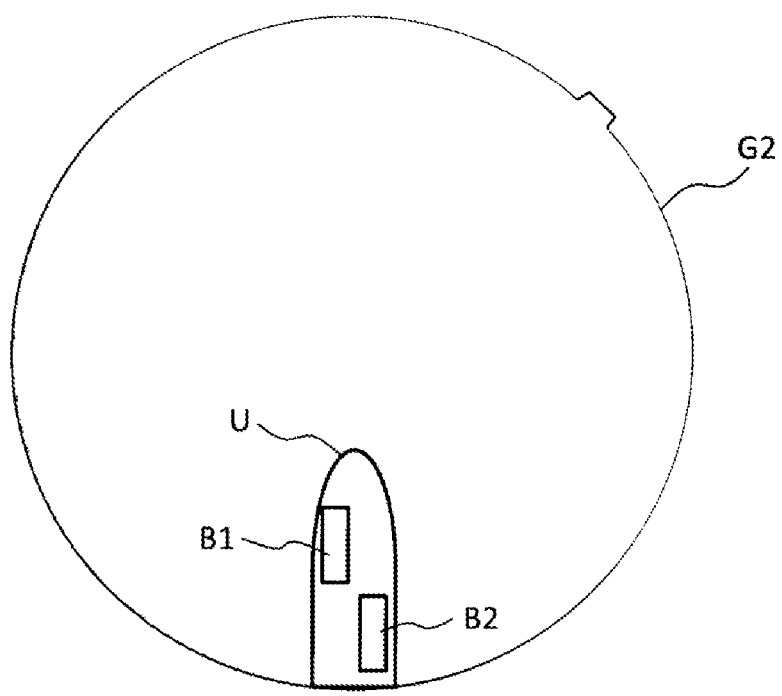
FIG. 5A is a schematic diagram for explaining processing performed by an ophthalmologic observation apparatus according to an embodiment.
Figure 5B:
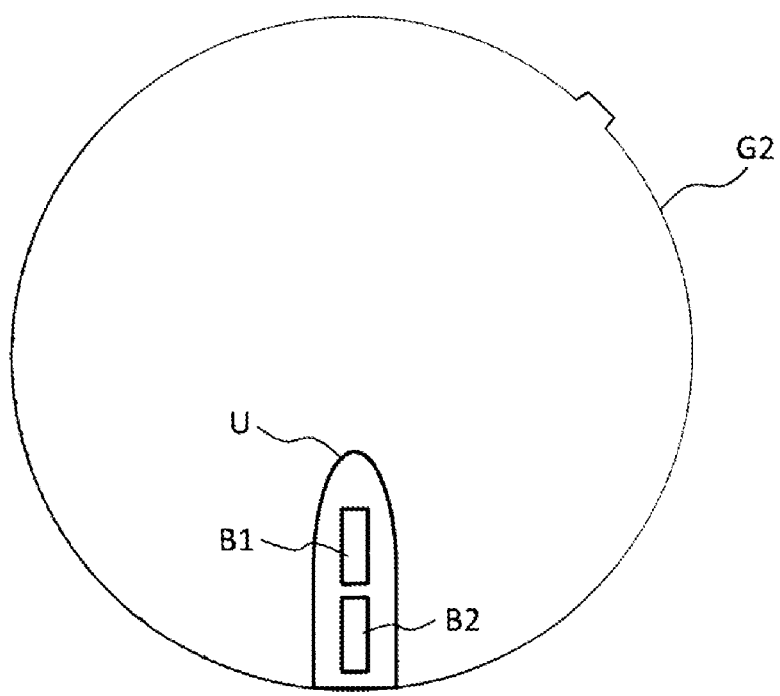
FIG. 5B is a schematic diagram for explaining processing performed by an ophthalmologic observation apparatus according to an embodiment.

An example of processing performed by the lens movement amount obtaining part 232 is descried. A front image input into the lens movement amount obtaining part 232 depicts the split index. An example of an aspect of depiction of the split index is illustrated in FIGS. 5A and 5B. An image of the fundus Ef is omitted in FIGS. 5A and 5B.

A shadow of the reflection rod 67 is depicted in a front image G2 of the fundus Ef illustrated in FIG. 5A, and two images (split index images) B1 and B2 of the split index are depicted as bright lines in a region of this shadow. Each of the split index images B1 and B2 are of substantially a rectangular shape.

If a focus position is displaced (in the z-direction), the split index images B1 and B2 are depicted such that they are displaced in a lateral direction from each other. A direction of the displacement thereof indicates a direction of the displacement of the focus position (+z-direction or −z-direction), and an amount of the displacement thereof indicates an amount of the displacement of the focus position. If a focus position is appropriate, the split index images B1 and B2 are depicted such that they aligns in a longitudinal direction with each other as illustrated in FIG. 5B.

The lens movement amount obtaining part 232 analyzes the front image G2 to find a shift of a focus position, and obtain a movement amount of the focusing lens 43 such that the shift is cancelled. Such processing may be performed in the following way, for example. To begin with, the lens movement amount obtaining part 232 specifies image regions corresponding to the split index images B1 and B2 based on pixel information (such as brightness values, etc.) of the front image G2. Next, the lens movement amount obtaining part 232 specifies a characteristic position (center, barycenter, axis line etc.) of the each image region specified. Then, the lens movement amount obtaining part 232 finds a lateral displacement between the characteristic positions of the two image regions corresponding to the split index images B1 and B2. Next, the lens movement amount obtaining part 232 calculates a shift of a focus position based on the found lateral displacement and obtains a movement amount of the focusing lens 43 such that this shift of the focus position is cancelled. Note that the lens movement amount obtaining part 232 may be configured to: store information that associates displacements of split index images defined in a coordinate system of a front image with shifts of a focus position defined in the real space in advance; and refer to such association information to find a shift of a focus position.

The lens movement amount obtaining part 232 may be configured to obtain a movement amount of the focusing lens 31 of the imaging optical system 30. This processing may be carried out by referring to association information like the above or by referring to information that associates focus positions of the focusing lens 31 with those of the focusing lens 43.

The optical path length difference change amount obtaining part 233 is described. When performing the optical path length difference adjustment between the signal light path and the reference light path, the ophthalmologic observation apparatus 1 controls the measuring optical system to perform OCT measurement of the fundus Ef. This OCT measurement is carried out by repetitively scanning the same cross section of the fundus Ef with a preset repetition frequency, for example. The optical path length difference change amount obtaining part 233 analyzes detection results of interference light LC acquired from this OCT measurement to obtain a change amount of an optical path length difference required for acquiring an image of a site of the fundus Ef at a determined depth (z-position). The optical path length difference change amount obtaining part 233 is an example of a "third obtaining part".

Information obtained by the optical path length difference change amount obtaining part 233 is not limited to a change amount of an optical path length difference itself. For example, the optical path length difference change amount obtaining part 233 may obtain information that is substantially equivalent to a change amount of an optical path length difference such as control contents (the number of pulses transmitted, or the like) of the optical path length changing part 41, information obtained in the middle of processing of acquiring the change amount (shift amount of a z-position of an image in a frame, etc.) or the like.

An example of processing performed by the optical path length difference change amount obtaining part 233 is descried. A cross-sectional image of a scanned cross section formed by the image forming part 220 is input into the optical path length difference change amount obtaining part 233, for example. The optical path length difference change amount obtaining part 233 analyzes pixel information (brightness values, etc.) of this cross-sectional image to obtain a z-position of a predetermined site of the fundus Ef in a frame. As an example of such processing, the optical path length difference change amount obtaining part 233 specifies an image region corresponding to a surface of the fundus Ef (boundary between a retina and a vitreous body), and finds a z-coordinate value of a characteristic site (a central fovea, an opening of an optic disk, etc.) in this image region. Next, the optical path length difference change amount obtaining part 233 finds a displacement of the z-coordinate value of the characteristic site from a predetermined reference z-coordinate value (center position in the z-direction in the frame), and obtains a change amount of the optical path length difference such that this displacement is cancelled. Note that the optical path length difference change amount obtaining part 233 may be configured to: store information that associates displacements in the z-direction defined in a coordinate system of a cross-sectional image with shifts of an optical path length difference defined in the real space in advance; and refer to such association information to find an optical path length difference.

The polarization change amount obtaining part 234 is described. When performing the polarization adjustment of signal light path and/or reference light, the ophthalmologic observation apparatus 1 performs detection of polarization (polarization direction) signal light LS and reference light LR. This detection includes, for example, processing of detecting polarization of reference light LR while obstructing the signal light path and processing of detecting polarization of signal light LS while obstructing the reference light path. Blockage of the signal light path may be carried out by controlling the galvano scanner 42, for example. Blockage of the reference light path may be carried out by controlling the optical attenuator 105.

Although illustration is omitted, it is possible to provide a detecting optical system configured to detect polarization. The detecting optical system may include, for example: an optical fiber whose one end is connected to an exit end of the fiber coupler 109 illustrated in FIG. 2; a polarizing plate arranged after the other end of this optical fiber; and a detecting element (photodiode, etc.) arranged after this polarizing plate. The polarizing plate is a polarizer that only transmits light with polarization in a specific direction, and rotated by an actuator (pulse motor, etc.: illustration omitted). Intensity of light detected by the detecting element varies in accordance with change in rotational position of the polarizing plate. A polarization direction in which the intensity of light detected becomes maximum is the polarization direction of the light. Note that it is possible to provide a rotatable polarizer as above in an arbitrary location between the exit end 111 of the optical fiber 110 and the CCD image sensor 115.

Information indicating the polarization direction of the signal light LS and information indicating the polarization direction of the reference light LR acquired in the above way are input into the polarization change amount obtaining part 234. The polarization change amount obtaining part 234 finds a displacement between the polarization direction of the signal light LS and the polarization direction of the reference light LR. This displacement is a displacement in a rotation direction (angle). Further, the polarization change amount obtaining part 234 obtains a change amount of polarization such that this displacement is cancelled.

The data processor 230 that functions as above includes, for example, the aforementioned microprocessor, RAM, ROM, hard disk drive, circuit boards, etc. Computer programs causing the microprocessor to execute the above functions are stored in storage devices such as the hard disk drive in advance.

(User Interface)

A user interface 240 includes the display 240A and operation part 240B. The display 240A includes a display device in the arithmetic and control unit 200 and/or display device 3. The operation part 240B includes operation devices in the arithmetic and control unit 200. The operation part 240B may include various buttons, keys, etc. provided on cases of the ophthalmologic observation apparatus 1 or outside thereof. For example, when the retinal camera unit 2 has a case similar to conventional retinal cameras, a joy stick, operation panel, etc. provided on this case may be included in the operation part 240B. The display 240A may include various display devices such as a touch panel etc. provided on the case of the retinal camera unit 2.

The display 240A and operation part 240B are not necessarily separate components. For example, like a touch panel, a compound device of display and operation functions may be applied. In this case, the operation part 240B includes the touch panel and computer programs. Contents of operation to the operation part 240B are input into the controller 210 as electrical signals. Further, operations and/or information input may be performed by means of graphical user interface (GUI) displayed on the display 240A and operation part 240B.

[Signal Light Scanning and OCT Images]

Now, scanning of signal light LS and OCT images are explained.

Scanning modes of the signal light LS by the ophthalmologic observation apparatus 1 may include, for example, horizontal, vertical, crossed, radial, circular, concentric, helical scans, etc. Taking observation site of fundus, analysis mode (retinal thickness etc.), time required for scanning, density of scanning, etc. into account, these scanning modes are selectively used.

The horizontal scan is one for scanning signal light LS in the horizontal direction (x-direction). The horizontal scan includes a mode of scanning signal light LS along multiple scanning lines extending in the horizontal direction and arranged in the vertical direction (y-direction). In this mode, the interval between scanning lines may be set arbitrarily. By setting the interval between adjacent scanning lines to be sufficiently narrow, three-dimensional image may be formed (three-dimensional scan). The vertical scan is performed in a similar manner.

The crossed scan is one for scanning signal light LS along a cross-shape trajectory consisting of two linear trajectories (line trajectories) orthogonal to each other. The radial scan is one for scanning signal light LS along a radial trajectory consisting of multiple line trajectories arranged at predetermined angles. The crossed scan is an example of the radial scan.

The circular scan is one for scanning signal light LS along a circular trajectory. The concentric scan is one for scanning signal light LS along multiple circular trajectories arranged concentrically around a predetermined center position. The circular scan is an example of the concentric scan. The helical scan is one for scanning signal light LS along a helical trajectory while making the turning radius gradually smaller (or greater).

Since the galvano scanner 42 is configured to scan signal light LS in the directions orthogonal to each other, the galvano scanner 42 is capable of scanning signal light LS in the x and y-directions independently. Signal light LS may be scanned along an arbitrary trajectory on the xy-plane by simultaneously controlling the orientations of two galvano mirrors included in the galvano scanner 42. As a result, various scanning modes as described above may be realized.

By scanning signal light LS in the modes described as above, it is possible to obtain a cross-sectional image in a plane spanned by the direction along a scanning line and the fundus depth direction (z-direction). Moreover, when the interval between scanning lines is narrow, a three-dimensional image may be obtained.

A region in the fundus Ef to be scanned by signal light LS as described above, that is, a region in the fundus Ef subject to OCT is referred to as a scanning region. A scanning region of three-dimensional scan is a rectangular region in which multiple horizontal scans are arranged. A scanning region of concentric scan is a disciform region surrounded by the trajectory of the circular scan with maximum diameter. A scanning region of radial scan is a disciform (or polygonal) region connecting ends of scanning lines.

[Operations]

Figure 6:
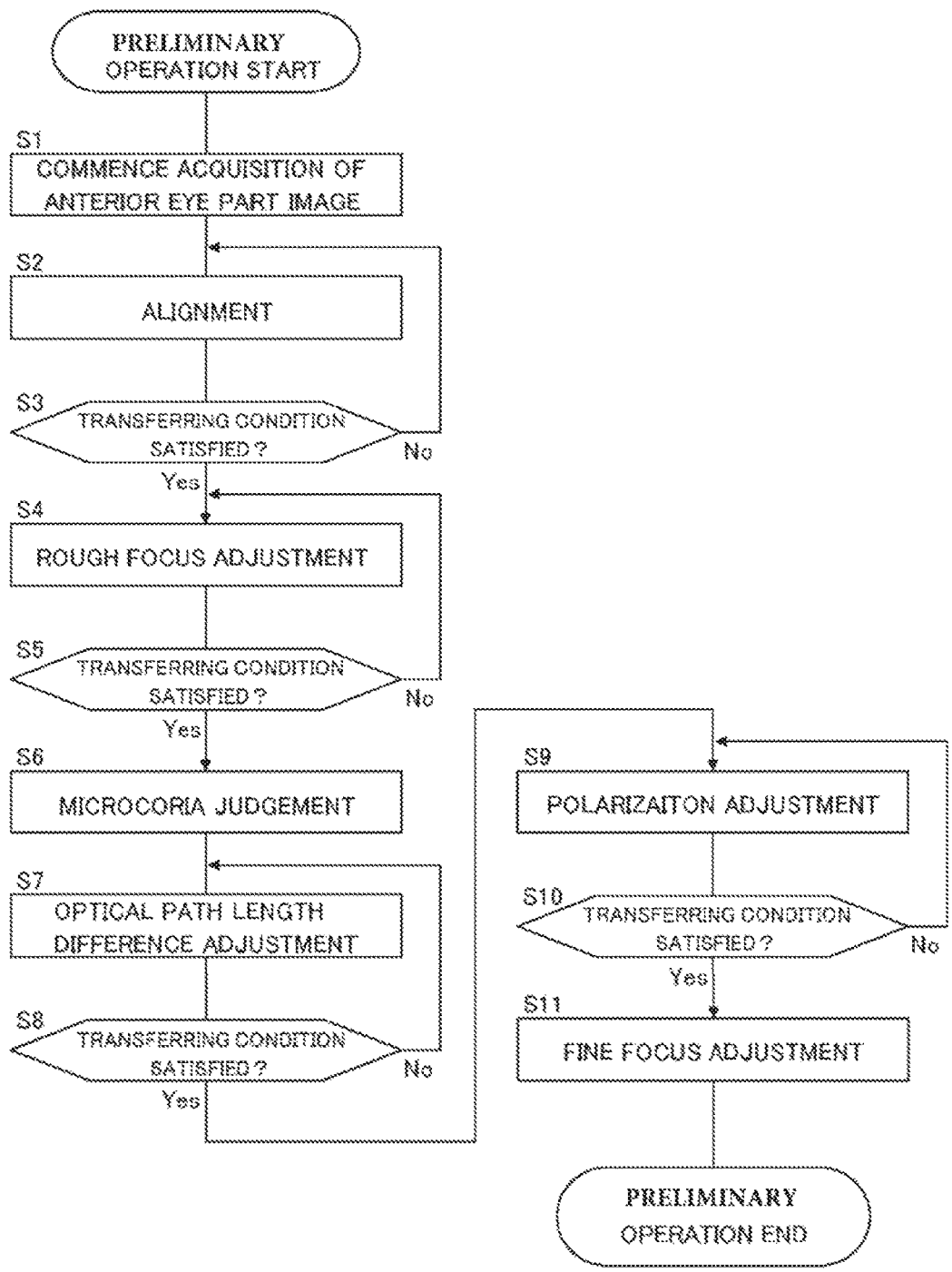
FIG. 6 is a flowchart representing an operation example of an ophthalmologic observation apparatus according to an embodiment.

Operations of the ophthalmologic observation apparatus 1 are described. FIG. 6 shows an example of processing performed by the ophthalmologic observation apparatus 1 in preliminary operations carried out before OCT measurement (and fundus photography). The present example describes a case in which alignment, rough focus adjustment, microcoria judgement, optical path length difference adjustment, polarization adjustment and fine focus adjustment are performed as preliminary operations in this order.

(S1: Commencing Acquisition of Anterior Eye Part Image)

To begin with, upon receiving a predetermined operation for commencing preliminary operations, the main controller 211 turns on the observation light source 11. With this, acquisition of a front image (near-infrared moving image) of the anterior eye part of the eye E is commenced. This front image is continuously acquired in real time until the observation light source 11 is turned off. The main controller 211 displays this front image as a moving image on the display 240A in real time.

(S2: Alignment)

The main controller 211 controls the alignment optical system 50 to project the alignment index onto the eye E. At this time, a fixation target is also projected onto the eye E by the LCD 39. The optical system movement amount obtaining part 231 analyzes frames (for example, all frames) acquired at preset time intervals to obtain a movement amount of the measuring optical system. The main controller 211 controls the optical system driver 500 to move the measuring optical system by the amount obtained. The main controller 211 repeatedly performs such processing.

(S3: Transferring Condition Satisfied?)

The main controller 211 judges whether or not the movement amount obtained in Step 2 satisfies the transferring condition for alignment, that is, whether or not the movement amount is smaller than the first threshold. Note that the alignment is continued until the terminating condition is satisfied, that is, until the movement amount becomes smaller than the second threshold.

(S4: Rough Focus Adjustment)

When the transferring condition is satisfied in Step 3 (S3: Yes), the main controller 211 commences the rough focus adjustment. Specifically, the main controller 211 executes control for commencing acquisition of a front image of the fundus Ef, and controls the focus optical system 60 to project the split index on the fundus Ef. The lens movement amount obtaining part 232 analyzes frames (for example, all frames) acquired at preset time intervals to obtain movement amounts of the focusing lens 31 and the focusing lens 43. The main controller 211 controls the photography focus driver 300 to move the focusing lens 31 by the movement amount and controls the OCT focus driver 400 to move the focusing lens 43 by the movement amount. The main controller 211 repeatedly performs such processing.

(S5: Transferring Condition Satisfied?)

The main controller 211 judges whether or not the movement amount obtained in Step 4 satisfies the transferring condition for rough focus adjustment, that is, whether or not the movement amount is smaller than the first threshold. Note that the rough focus adjustment is continued until the terminating condition is satisfied, that is, until the movement amount becomes smaller than the second threshold.

(S6: Microcoria Judgement)

When the transferring condition is satisfied in Step 5 (S5: Yes), the main controller 211 performs the microcoria judgement. The microcoria judgement includes, for example, acquisition of a front image (anterior eye part image) of the eye E, judgement processing, and control of the diaphragm 19. Note that a front image to be analyzed may be one acquired in Step 1 etc.

(S7: Optical Path Length Difference Adjustment)

After finishing the microcoria judgement, the main controller 211 performs control for commencing the optical path length difference adjustment. Specifically, the main controller 211 controls the measuring optical system to detect interference light LC. The optical path length difference change amount obtaining part 233 analyzes interference light LC (for example, interference light LC corresponding to one frame) acquired at preset time intervals to obtain a change amount of the optical path length difference between the signal light path and the reference light path. The main controller 211 controls the optical path length changing part 41 to change the optical path length of the signal light path by the change amount. With this, the optical path length difference between the signal light path and the reference light path is varied by this change amount. The main controller 211 repeatedly performs such processing.

(S8: Transferring Condition Satisfied?)

The main controller 211 judges whether or not the change amount obtained in Step 7 satisfies the transferring condition for optical path length difference adjustment, that is, whether or not the movement amount is smaller than the first threshold. Note that the optical path length difference adjustment is continued until the terminating condition is satisfied, that is, until the change amount becomes smaller than the second threshold.

(S9: Polarization Adjustment)

When the transferring condition is satisfied in Step 8 (S8: Yes), the main controller 211 commences the polarization adjustment. Specifically, the main controller 211 executes control the measuring optical system and the detecting optical system to detect a polarization direction of the signal light LS and a polarization direction of the reference light LR. The polarization change amount obtaining part 234 analyzes interference light LC (for example, interference light LC corresponding to one frame or one A-line) acquired at preset time intervals to obtain a change amount of the polarization direction. The main controller 211 controls the polarization controller 106 to change the polarization direction of the reference light LR by the change amount. With this, a relative polarization direction between the signal light LS and the reference light LR I changed by the change amount. The main controller 211 repeatedly performs such processing.

(S10: Transferring Condition Satisfied?)

The main controller 211 judges whether or not the movement amount obtained in Step 9 satisfies the transferring condition for polarization adjustment, that is, whether or not the movement amount is smaller than the first threshold. Note that the polarization adjustment is continued until the terminating condition is satisfied, that is, until the movement amount becomes smaller than the second threshold.

(S11: Fine Focus Adjustment)

When the transferring condition is satisfied in Step 10 (S10: Yes), the main controller 211 commences the fine focus adjustment. The fine focus adjustment is performed, for example, by: monitoring interference intensity (interference sensitivity) by carrying out OCT measurement of the eye E and acquiring interference signals; finding a position of the focusing lens 43 at which the interference intensity is maximized; and moving the focusing lens 43 to the position found.

When all the preliminary operations including the fine focus adjustment is completed, the preliminary operations end. The main controller 211 receives a predetermined trigger and performs control for OCT measurement of the fundus Ef (main measurement, actual measurement). The description of the present operation example ends here.

FIG. 7 illustrates an example of a time course of preliminary operations like above. The time course of the present example is shown in the following.

Time t=0: Commencement of alignment
Time t=t1: Commencement of rough focus adjustment in the middle of alignment
Time t=t2: Termination of alignment
Time t=t3: Commencement of microcoria adjustment in the middle of rough focus adjustment
Time t=t4: Termination of rough focus adjustment
Time t=t5: Termination of microcoria adjustment and commencement of optical path length difference adjustment
Time t=t6: Commencement of polarization adjustment in the middle of optical path length difference adjustment
Time t=t7: Termination of optical path length difference adjustment
Time t=t8: Commencement of fine focus adjustment in the middle of polarization adjustment
Time t=t7: Termination of polarization adjustment
Time t=t8: Termination of fine focus adjustment According to the present operation example, in comparison with a case in which these preliminary operations are sequentially performed one by one, operation time is shortened by an amount corresponding to overlaps of execution periods of different preliminary operations, that is, by an amount corresponding to parallel executions of different preliminary operations. Specifically, a time required for the preliminary operations is shortened by an amount "(t2−t1)+(t4−t3)+(t7−t6)+(t9−t8)" in comparison with a case in which these preliminary operations are performed in a serial manner.

Note that regarding any kind of preliminary operation, a transferring condition (first threshold) and a terminating condition (second threshold) may be set arbitrarily. In general, the larger a difference between a first threshold and a second threshold becomes, the larger an expected effect of time savings becomes. Further, there are cases in which a result of a preliminary operation is utilized for a different preliminary operation in a post stage. For example, it is difficult to perform rough focus adjustment unless alignment is appropriate to a certain extent. Thus, it is desired to set a first threshold and a second threshold while taking various factors into account.

[Effects]

Effects of the ophthalmologic observation apparatus 1 are explained.

The ophthalmologic observation apparatus 1 includes a measuring optical system, an image forming part, a preliminary operation performing part, a storage, and a controller.

The measuring optical system is used for OCT measurement of the eye E, and includes an optical system included in the OCT unit 100 and an optical system in the retinal camera unit 2 that forms a signal light path.

The image forming part forms an image of the eye E based on information acquired by OCT measurement, and includes the image forming part 220.

The preliminary operation performing part performs a plurality of preliminary operations for executing OCT measurement, and includes components in accordance with types of preliminary operations as described above.

The storage stores, for at least one specific preliminary operation among the plurality of preliminary operations, operating condition information (212a) including a transferring condition for transferring to a different preliminary operation and a terminating condition for terminating a specific preliminary operation in advance, and includes the storage 212.

The controller includes the main controller 211, and executes the following processing: controlling the preliminary operation performing part to commence a specific preliminary operation; controlling the preliminary operation performing part to commence a different preliminary operation when the transferring condition of this specific preliminary operation is satisfied; and controlling the preliminary operation performing part to terminate this specific preliminary operation when the terminating condition of this specific preliminary operation is satisfied.

Embodiments relating to various types of preliminary operations may be realized by the following configurations.

Described is a case in which a specific preliminary operation is alignment of the measuring optical system with respect to the eye E. The preliminary operation performing part includes the following components: a first projection optical system (alignment optical system 50) configured to project a first index (alignment index) for alignment onto the eye E; a photographing optical system (illumination optical system 10 and imaging optical system 30) configured to photograph the eye E on which the first index is being projected to acquire a front image; a first driver (optical system driver 500) configured to move the measuring optical system; and a first obtaining part (optical system movement amount obtaining part 231) configured to analyze the front image to obtain a movement amount of the measuring optical system.

The storage stores a first threshold of a movement amount of the measuring optical system as the transferring condition and a second threshold that is smaller than the first threshold as the terminating condition.

After controlling the preliminary operation performing part to commence alignment, the controller performs control for commencing a different preliminary operation when the movement amount obtained by the first obtaining part becomes equal to or less than the first threshold. Further, the controller performs control for terminating the alignment when the movement amount obtained by the first obtaining part becomes equal to or less than the second threshold.

Described is a case in which a specific preliminary operation is focus adjustment of the measuring optical system with respect to the eye E. The measuring optical system includes a focusing lens 43 that is movable in an optical axis direction.

The preliminary operation performing part includes the following components: a second projection optical system (focus optical system 60) configured to project a second index for focus adjustment onto the eye E; a photographing optical system (illumination optical system 10 and imaging optical system 30) configured to photograph the eye E on which the second index is being projected to acquire a front image; a second driver (OCT focus driver 400) configured to move the focusing lens 43; and a second obtaining part (lens movement amount obtaining part 232) configured to analyze the front image to obtain a movement amount of the focusing lens 43.

The storage stores a first threshold of a movement amount of the focusing lens 43 as the transferring condition and a second threshold that is smaller than the first threshold as the terminating condition.

After controlling the preliminary operation performing part to commence focus adjustment, the controller performs control for commencing a different preliminary operation when the movement amount obtained by the second obtaining part becomes equal to or less than the first threshold. Further, the controller performs control for terminating the focus adjustment when the movement amount obtained by the second obtaining part becomes equal to or less than the second threshold.

Described is a case in which a specific preliminary operation is adjustment of an optical path length difference between signal light and reference light. The measuring optical system splits light from a light source (light source unit 101) into signal light LS and reference light LR, and detects interference light LC of the signal light LS traveled via the eye E and the reference light LR traveled via a reference light path.

The preliminary operation performing part includes the following components: an optical path length difference changing part (optical path length changing part 41) configured to change an optical path length difference between the signal light LS and the reference light LR, that is, an optical path length difference between the signal light path and the reference light path; and a third obtaining part (optical path length difference change amount obtaining part 233) configured to analyze detection results of interference light LC from the measuring optical system to obtain a change amount of the optical path length difference.

The storage stores a first threshold of a change amount of the optical path length difference as the transferring condition and a second threshold that is smaller than the first threshold as the terminating condition.

After controlling the preliminary operation performing part to commence adjustment of the optical path length difference, the controller performs control for commencing a different preliminary operation when the change amount obtained by the third obtaining part becomes equal to or less than the first threshold. Further, the controller performs control for terminating the adjustment of the optical path length difference when the change amount obtained by the third obtaining part becomes equal to or less than the second threshold.

Described is a case in which a specific preliminary operation is adjustment of polarization of signal light and/or reference light. The measuring optical system splits light from a light source (light source unit 101) into signal light LS and reference light LR, and detects interference light LC of the signal light LS traveled via the eye E and the reference light LR traveled via a reference light path.

The preliminary operation performing part includes the following components: a polarization changing part (polarization controller 106) configured to change polarization of the signal light LS and/or the reference light LR; and a fourth obtaining part (polarization change amount obtaining part 234) configured to analyze detection results of interference light LC from the measuring optical system to obtain a change amount of the polarization.

The storage stores a first threshold of a change amount of polarization as the transferring condition and a second threshold that is smaller than the first threshold as the terminating condition.

After controlling the preliminary operation performing part to commence polarization adjustment, the controller performs control for commencing a different preliminary operation when the change amount obtained by the fourth obtaining part becomes equal to or less than the first threshold. Further, the controller performs control for terminating the polarization adjustment when the change amount obtained by the fourth obtaining part becomes equal to or less than the second threshold.

With the embodiments described above, a different preliminary operation may be started before a specific preliminary operation. Thus, it is capable of executing at least part of the specific preliminary operation and at least part of the different preliminary operation in parallel. Accordingly, it is possible to shorten a time required for preparation for OCT.

[Modification Examples]

The configurations described above are merely illustrations for favorably implementing the present invention. Therefore, it is possible to make arbitrary modifications (omission, replacement, addition, etc.) within the scope of the present invention.

Computer programs for implementing the above embodiments may be stored in any kinds of computer-readable recording media. Examples of such recording media include an optical disk, semiconductor memory, magneto-optic disk (CD-ROM, DVD-RAM, DVD-ROM, MO, etc.), magnetic storage (a hard disk, a floppy Disk™, ZIP, etc.), etc.

The programs may be transmitted through networks such as internet, LAN, etc.

The invention claimed is:

1. An ophthalmologic observation apparatus comprising:
an optical coherence tomography unit, including a focusing lens that is movable in an optical axis direction, the optical coherence tomography unit configured to perform optical coherence tomography of an eye;
an image forming circuit board configured to form data representative of an image of the eye based on information acquired by the optical coherence tomography;
a controller including a microprocessor that is configured to control a subsystem to perform a plurality of preliminary operations for optical coherence tomography, the subsystem comprising one or more of
(a) an alignment optical system comprising a plurality of optical elements, arranged to project a first index for alignment onto the eye;
an illumination optical system and an imaging optical system, collectively comprising a plurality of optical elements arranged to photograph the eye on which the first index is being projected to acquire a front image;
a first driver including a motor configured to move the optical coherence tomography unit; and
wherein the microprocessor is configured to analyze the front image to obtain a movement amount of the optical coherence tomography unit; or
(b) a focus optical system comprising a plurality of optical elements arranged to project a second index for focus adjustment onto the eye;
wherein the plurality of optical elements of the illumination optical system and the imaging optical system are arranged to photograph the eye on which the second index is being projected to acquire the front image;
a second driver including a motor configured to move the focusing lens; and
wherein the microprocessor is configured to analyze the front image to obtain the movement amount of the focusing lens; or
(c) a retinal camera or a scanning laser ophthalmoscope configured to change an optical path length difference; and
wherein the microprocessor is configured to analyze a detection result of the interference light from the optical coherence tomography unit to obtain a change amount of the optical path length difference; or
(d) a polarization controller including an optical fiber and configured to induce stress in the optical fiber to change polarization of the signal light and/or the reference light; and
wherein the microprocessor is configured to analyze the detection result of the interference light from the optical coherence tomography unit to obtain a change amount of the polarization;
a computer-readable recording media storing, for at least one specific preliminary operation among the plurality of preliminary operations, operating condition information including a transferring condition for transferring to a different preliminary operation, the transferring condition representing a condition for commencing the different preliminary operation when satisfied, and a terminating condition for terminating a specific preliminary operation, wherein the transferring condition and the terminating condition associated with the plurality of preliminary operations performed by the ophthalmologic apparatus are pre-set, such that the terminating condition of the at least one specific preliminary operation is not satisfied unless the transferring condition is satisfied; and the controller, including the microprocessor, configured:
to commence a specific preliminary operation,
to commence a different preliminary operation in response to the transferring condition of the specific preliminary operation being satisfied, and
to terminate the specific preliminary operation in response to the terminating condition of the specific preliminary operation being satisfied,
wherein the terminating condition is preset to not be satisfied unless the transferring condition has been satisfied such that the different preliminary operation is commenced prior to the specific preliminary operation being terminated,
wherein the transferring condition is one or more of:
  detecting a threshold movement amount of the optical coherence tomography unit;
  detecting a threshold movement amount of the focusing lens;
  detecting a threshold change amount of the optical path length difference;
  detecting a threshold change amount of the polarization; and
  detecting a threshold change amount of interference intensity.

2. The ophthalmologic observation apparatus of claim 1, wherein
the specific preliminary operation includes the controller controlling the subsystem comprising the alignment optical system, the illumination optical system, and the imaging optical system to perform alignment of the optical coherence tomography unit with respect to the eye,
further wherein the computer-readable recording media stores a first threshold of the movement amount of the optical coherence tomography unit obtained by the microprocessor based the front image as the transferring condition and a second threshold that is smaller than the first threshold as the terminating condition, and
during the alignment of the optical coherence tomography unit is performed, the controller controls to the subsystem to commence the different preliminary operation when the movement amount obtained by the microprocessor becomes equal to or less than the first threshold, and controls the subsystem to terminate the alignment when the movement amount becomes equal to or less than the second threshold.

3. The ophthalmologic observation apparatus of claim 1, wherein
the specific preliminary operation includes the controller controlling the subsystem comprising the focus optical system, the illumination optical system, and the imaging optical system to perform focus adjustment of the optical coherence tomography unit with respect to the eye,
further wherein the computer-readable recording media stores a first threshold of the movement amount of the focusing lens obtained by the microprocessor based on front image as the transferring condition and a second threshold that is smaller than the first threshold as the terminating condition, and
during the focus adjustment of the optical coherence tomography unit, the controller controls the subsystem to commence the different preliminary operation when the movement amount obtained by the data processor becomes equal to or less than the first threshold, and controls the subsystem to terminate the focus adjustment when the movement amount becomes equal to or less than the second threshold.

4. The ophthalmologic observation apparatus of claim 1, wherein
the optical coherence tomography unit splits light from a light source into signal light and reference light, and detects interference light of the signal light traveled via the eye and the reference light traveled via a reference light path,
the specific preliminary operation includes the controller controlling the subsystem comprising the subsystem comprising a retinal camera or a scanning laser ophthalmoscope to perform adjustment of an optical path length difference between the signal light and the reference light,
further wherein, the computer-readable recording media stores a first threshold of the change amount of the optical path length difference obtained by the microprocessor based on the detection result of the interference light as the transferring condition and a second threshold that is smaller than the first threshold as the terminating condition, and
during the adjustment of the optical path length difference between the signal light and the reference light, the controller controls the subsystem to commence the different preliminary operation when the change amount obtained by the data processor becomes equal to or less than the first threshold, and controls the subsystem to terminate the adjustment of the optical path length difference when the change amount becomes equal to or less than the second threshold.

5. The ophthalmologic observation apparatus of claim 1, wherein
the optical coherence tomography unit splits light from a light source into signal light and reference light, and detects interference light of the signal light traveled via the eye and the reference light traveled via a reference light path,
the specific preliminary operation includes the controller controlling the subsystem comprising the polarization controller to perform polarization adjustment of at least one of the signal light and the reference light,
further wherein the computer-readable recording media stores a first threshold of the change amount of the polarization detected by the microprocessor based on the detection result of the interference light as the transferring condition and a second threshold that is smaller than the first threshold as the terminating condition, and
during the polarization adjustment, the controller controls the subsystem to commence the different preliminary operation when the change amount obtained by the data processor becomes equal to or less than the first threshold, and controls the subsystem to terminate the polarization adjustment when the change amount becomes equal to or less than the second threshold.

6. A method of operating an ophthalmologic observation apparatus to perform optical coherence tomography of an eye by an optical coherence tomography unit and form an image of the eye based on information acquired by the optical coherence tomography, the method comprising:
performing a plurality of preliminary operations for optical coherence tomography;
storing, for at least one specific preliminary operation among the plurality of preliminary operations, operating condition information including a transferring condition for transferring to a different preliminary operation and a terminating condition for terminating a specific preliminary operation, the transferring condition representing a condition for commencing the different preliminary operation when satisfied, wherein the transferring condition and the terminating condition are pre-set such that the terminating condition is not satisfied unless the transferring condition is satisfied; and controlling one of the preliminary operations to,
- commence a specific preliminary operation,
- control the preliminary operation performing to commence a different preliminary operation in response to the transferring condition of the specific preliminary operation being satisfied, and
- control the preliminary operation performing to terminate the specific preliminary operation in response to the terminating condition of the specific preliminary operation being satisfied, wherein the terminating condition is preset to not be satisfied unless the transferring condition has been satisfied such that the different preliminary operation is commenced prior to the specific preliminary operation being terminated;

wherein the transferring condition is one or more of:
- detecting a threshold movement amount of the optical coherence tomography unit;
- detecting a threshold movement amount of a focusing lens;
- detecting a threshold change amount of an optical path length difference;
- detecting a threshold change amount of a polarization; and
- detecting a threshold change amount of interference intensity.

7. The method of claim 6, wherein
the specific preliminary operation comprises aligning the optical coherence tomography unit with respect to the eye,
the preliminary operation performing comprising:
projecting a first index for alignment onto the eye;
photographing the eye on which the first index is being projected to acquire a front image;
moving the optical coherence tomography unit; and
analyzing the front image to obtain a movement amount of the optical coherence tomography unit,
storing a first threshold of the movement amount as the transferring condition and a second threshold that is smaller than the first threshold as the terminating condition, and
during the alignment, commencing the different preliminary operation when the movement amount becomes equal to or less than the first threshold, and terminating the alignment when the movement amount becomes equal to or less than the second threshold.

8. The method of claim 6, further comprising:
providing the focusing lens that is movable in an optical axis direction,
the specific preliminary operation including performing focus adjustment of the optical coherence tomography unit with respect to the eye,
the preliminary operation performing comprising:
projecting a second index for focus adjustment onto the eye;
photographing the eye on which the second index is being projected to acquire a front image;
moving the focusing lens; and
analyzing the front image to obtain a movement amount of the focusing lens, storing a first threshold of the movement amount as the transferring condition and a second threshold that is smaller than the first threshold as the terminating condition, and
during the focus adjustment, commencing the different preliminary operation when the movement amount becomes equal to or less than the first threshold, and terminating the focus adjustment when the movement amount becomes equal to or less than the second threshold.

9. The method of claim 6, wherein optical coherence tomography unit splits light from a light source into signal light and reference light, and detects interference light of the signal light traveled via the eye and the reference light traveled via a reference light path,
the specific preliminary operation includes adjusting an optical path length difference between the signal light and the reference light,
the preliminary operation performing comprises:
changing the optical path length difference; and
analyzing a detection result of the interference light from the optical coherence tomography unit to obtain a change amount of the optical path length difference,
storing a first threshold of the change amount as the transferring condition and a second threshold that is smaller than the first threshold as the terminating condition, and
during the adjustment of the optical path length difference, commending the different preliminary operation when the change amount becomes equal to or less than the first threshold, and terminating the adjustment of the optical path length difference when the change amount becomes equal to or less than the second threshold.

10. The method of claim 6, wherein the optical coherence tomography unit splitting light from a light source into signal light and reference light, and detecting interference light of the signal light traveled via the eye and the reference light traveled via a reference light path,
the specific preliminary operation includes performing polarization adjustment of the signal light and/or the reference light,
the preliminary operation performing comprises:
changing polarization of the signal light and/or the reference light; and
analyzing a detection result of the interference light from the optical coherence tomography unit to obtain a change amount of the polarization,
storing a first threshold of the change amount as the transferring condition and a second threshold that is smaller than the first threshold as the terminating condition, and
during the polarization adjustment, commencing the different preliminary operation when the change amount becomes equal to or less than the first threshold, and terminating the polarization adjustment when the change amount becomes equal to or less than the second threshold.

* * * * *